United States Patent
Uozumi (10) Patent No.: US 9,845,454 B2
(45) Date of Patent: Dec. 19, 2017

(54) CULTURE APPARATUS, CULTURE APPARATUS SYSTEM, CULTURE OPERATION MANAGEMENT METHOD, AND NON-TRANSITORY STORAGE MEDIUM STORING PROGRAM

(71) Applicant: NIKON CORPORATION, Tokyo (JP)

(72) Inventor: Takayuki Uozumi, Machida (JP)

(73) Assignee: NIKON CORPORATION, Tokyo (JP)

( * ) Notice: Subject to any disclaimer, the term of this patent is extended or adjusted under 35 U.S.C. 154(b) by 11 days.

(21) Appl. No.: 14/031,605

(22) Filed: Sep. 19, 2013

(65) Prior Publication Data

US 2014/0057342 A1 Feb. 27, 2014

Related U.S. Application Data

(63) Continuation of application No. PCT/JP2012/002043, filed on Mar. 23, 2012.

(30) Foreign Application Priority Data

Mar. 24, 2011 (JP) .................................. 2011-066648

(51) Int. Cl.
*C12M 1/34* (2006.01)
*C12M 1/36* (2006.01)

(52) U.S. Cl.
CPC ............ *C12M 41/46* (2013.01); *C12M 41/36* (2013.01); *C12M 41/48* (2013.01)

(58) Field of Classification Search
CPC ....... C12M 41/46; C12M 41/36; C12M 41/48
See application file for complete search history.

(56) References Cited

U.S. PATENT DOCUMENTS

| | | |
|---|---|---|
| 2005/0282268 A1 | 12/2005 | Kagayama |
| 2007/0281351 A1 | 12/2007 | Kobayashi et al. |
| 2009/0042293 A1 | 2/2009 | Hata et al. |
| 2009/0081769 A1 | 3/2009 | Kiyota et al. |

(Continued)

FOREIGN PATENT DOCUMENTS

| | | |
|---|---|---|
| EP | 2 213 722 A1 | 8/2010 |
| JP | A-2005-304302 | 11/2005 |
| JP | A-2005-304303 | 11/2005 |

(Continued)

OTHER PUBLICATIONS

Nov. 14, 2014 Extended Search Report issued in European Application No. 12761169.7.

(Continued)

*Primary Examiner* — Gautam Prakash
(74) *Attorney, Agent, or Firm* — Oliff PLC (57) ABSTRACT

A culture apparatus includes a culture unit which cultures cells under a predetermined culture environment, and an imaging unit which captures an inspection image showing a state of a culture container which holds the cells or a state of the cells, further includes a carrying unit and a determining unit. The carrying unit delivers the culture container between at least one peripheral device to be used in a culture operation of the cells and the culture apparatus. The determining unit detects completion of the culture operation of the peripheral device, controls the imaging unit to capture the inspection image, and analyzes the inspection image to determine whether or not the culture operation by the peripheral device is appropriate.

21 Claims, 4 Drawing Sheets

(56) References Cited

U.S. PATENT DOCUMENTS

| | | |
|---|---|---|
| 2010/0291663 A1 | 11/2010 | Koshiba |
| 2011/0013821 A1 | 1/2011 | Mimura et al. |

FOREIGN PATENT DOCUMENTS

| | | |
|---|---|---|
| JP | A-2006-11415 | 1/2006 |
| JP | A-2007-110932 | 5/2007 |
| JP | 2007-295827 A | 11/2007 |
| JP | A-2007-319119 | 12/2007 |
| JP | 2010099011 A | 5/2010 |
| WO | 2007052716 A | 3/2007 |
| WO | WO 2007/136073 A1 | 11/2007 |
| WO | WO 2009/093585 A1 | 7/2009 |

OTHER PUBLICATIONS

Jan. 20, 2015 Office Action issued in Japanese Patent Application No. 2013-505825.

Hiroto Sasaki et al., "Prediction of the degree of damage in a cell during one-generation-to-next-generation incubation based on cell image analysis," Regenerative Medicine, Journal of Japanese Society for Regenerative Medicine, 2011, vol. 10, pp. 157, O-13-3.

Ryuuji Kato et al., "Method for classification of various kinds of cells using image analysis for cell quality inspection," Regenerative Medicine, Journal of Japanese Society for Regenerative Medicine, 2011, vol. 10, pp. 157, O-13-1.

Sep. 24, 2013 International Preliminary Report on Patentability issued in International Patent Application No. PCT/JP2012/002043.

May 15, 2012 International Search Report issued in International Patent Application No. PCT/JP2012/002043.

Sep. 8, 2015 Decision on Refusal issued in Japanese Patent Application No. 2013-505825.

Oct. 5, 2015 Office Action issued in European Patent Application No. 12 761 169.7.

Feb. 8, 2016 Reconsideration Report issued in Japanese Patent Application No. 2013-505825.

Aug. 19, 2016 Office Action issued in European Patent Application No. 12761169.7.

Feb. 29, 2016 Office Action issued in European Patent Application No. 12761169.7.

Dec. 13, 2016 Office Action issued in Japanese patent application No. 2013-505825.

Jan. 19, 2017 Office Action issued in European patent application No. 12761169.7-1402.

Oct. 25, 2017 Office Action issued in European Patent Application No. 12761169.7.

FIG.1

CULTURE OPERATION INFORMATION ON CULTURE CONTAINER A

| DATE AND TIME | TYPE OF CULTURE OPERATION | PROPRIETY | FILE NAME OF INSPECTION IMAGE |
|---|---|---|---|
| 2011.02.01 10:00 | WASHER | APPROPRIATE | PIC00001.bmp |
| 2011.02.01 10:05 | DISPERNSER | APPROPRIATE | PIC00002.bmp |
| 2011.02.02 08:30 | WASHER | APPROPRIATE | PIC00003.bmp |
| 2011.02.02 08:35 | DISPERNSER | APPROPRIATE | PIC00004.bmp |
| 2011.02.02 15:00 | WASHER | APPROPRIATE | PIC00005.bmp |
| 2011.02.02 15:05 | CELL PICKER | APPROPRIATE | PIC00006.bmp |

CULTURE APPARATUS, CULTURE APPARATUS SYSTEM, CULTURE OPERATION MANAGEMENT METHOD, AND NON-TRANSITORY STORAGE MEDIUM STORING PROGRAM

CROSS-REFERENCE TO RELATED APPLICATION

This application is a continuation application of International Application PCT/JP2012/002043, filed Mar. 23, 2012, designating the U.S., and claims the benefit of priority from Japanese Patent Application No. 2011-066648, filed on Mar. 24, 2011, the entire contents of which are incorporated herein by reference.

BACKGROUND

1. Field

The present teachings relate to a culture apparatus, a culture apparatus system, a culture operation management method, and a non-transitory storage medium storing program.

2. Description of the Related Art

A technology for industrially managing the quality of culture cells is recognized as a base technology for an advanced medical field, a drug discovery field, and the like. As an example, in a regenerative medicine field, in order to generate a desired cell tissue, there is a culture process that proliferates and differentiates stem cells (iPS cells and ES cells) in vitro. Since the cell tissue generated in the culture process described above is assumed to be returned to a human body, the quality management of the culture cells in the culture process is very important issue. As an example, various apparatuses that perform time-lapse observation on the culture cells are proposed (for example, see Japanese Unexamined Patent Application Publication No. 2006-11415).

SUMMARY

A culture apparatus according to one aspect of the present teachings includes a culture unit which cultures cells under a predetermined culture environment, and an imaging unit which captures an inspection image showing a state of a culture container which holds the cells or a state of the cells, further includes a carrying unit and a determining unit. The carrying unit delivers the culture container between at least one peripheral device to be used in a culture operation of the cells and the culture apparatus. The determining unit detects completion of the culture operation of the peripheral device, controls the imaging unit to capture the inspection image, and analyzes the inspection image to determine whether or not the culture operation by the peripheral device is appropriate.

A culture apparatus according to another aspect of the present teachings includes a culture unit which cultures cells under a predetermined culture environment, and an imaging unit which captures an inspection image showing a state of a culture container which holds the cells or a state of the cells, further includes a culture operation control unit and a determining unit. The culture operation control unit operates at least one peripheral device to be used in a culture operation of the cells. The determining unit detects completion of the culture operation of the peripheral device by the culture operation control unit, controls the imaging unit to capture the inspection image, and analyzes the inspection image to determine whether or not the culture operation by the peripheral device is appropriate.

A culture apparatus system according to another aspect of the present teachings includes a culture unit which cultures cells under a predetermined culture environment; at least one peripheral device to be used in a culture operation of the cells; an imaging unit which captures an inspection image showing a state of a culture container which holds the cells or a state of the cells at least after a culture operation is performed on the cells; a determining unit which analyzes the inspection image to determine whether or not the culture operation is appropriate; and a control unit which controls the culture unit, the peripheral device, the imaging unit, and the determining unit.

A culture operation management method being applied to a culture apparatus system according to another aspect of the present teachings includes a culture unit culturing cells under a predetermined culture environment; and an imaging unit capturing an inspection image showing one of a state of a culture container which holds the cells and a state of the cells, in which the method includes the steps of detecting that a culture operation was performed by at least one peripheral device to be used in the culture operation of the cells; capturing, by the imaging unit, the inspection image showing one of the state of the culture container which holds the cells and the state of the cells after a performance of the culture operation by the peripheral device is detected in the step of detecting; and analyzing the inspection image to determine whether or not the culture operation is appropriate.

A non-transitory storage medium storing a program causing a computer to control a culture apparatus system according to another aspect of the present teachings includes a culture unit culturing cells under a predetermined culture environment; and an imaging unit capturing an inspection image showing one of a state of a culture container which holds the cells and a state of the cells, and the non-transitory storage medium storing the program causing the computer to execute the steps of detecting that a culture operation was performed by at least one peripheral device to be used in the culture operation of the cells; capturing, by the imaging unit, the inspection image showing one of the state of the culture container which holds the cells and the state of the cells after a performance of the culture operation by the peripheral device is detected in the step of detecting; and analyzing the inspection image to determine whether or not the culture operation is appropriate.

DETAILED DESCRIPTION OF THE EMBODIMENTS

<Explanation of One Embodiment>

Figure 1:
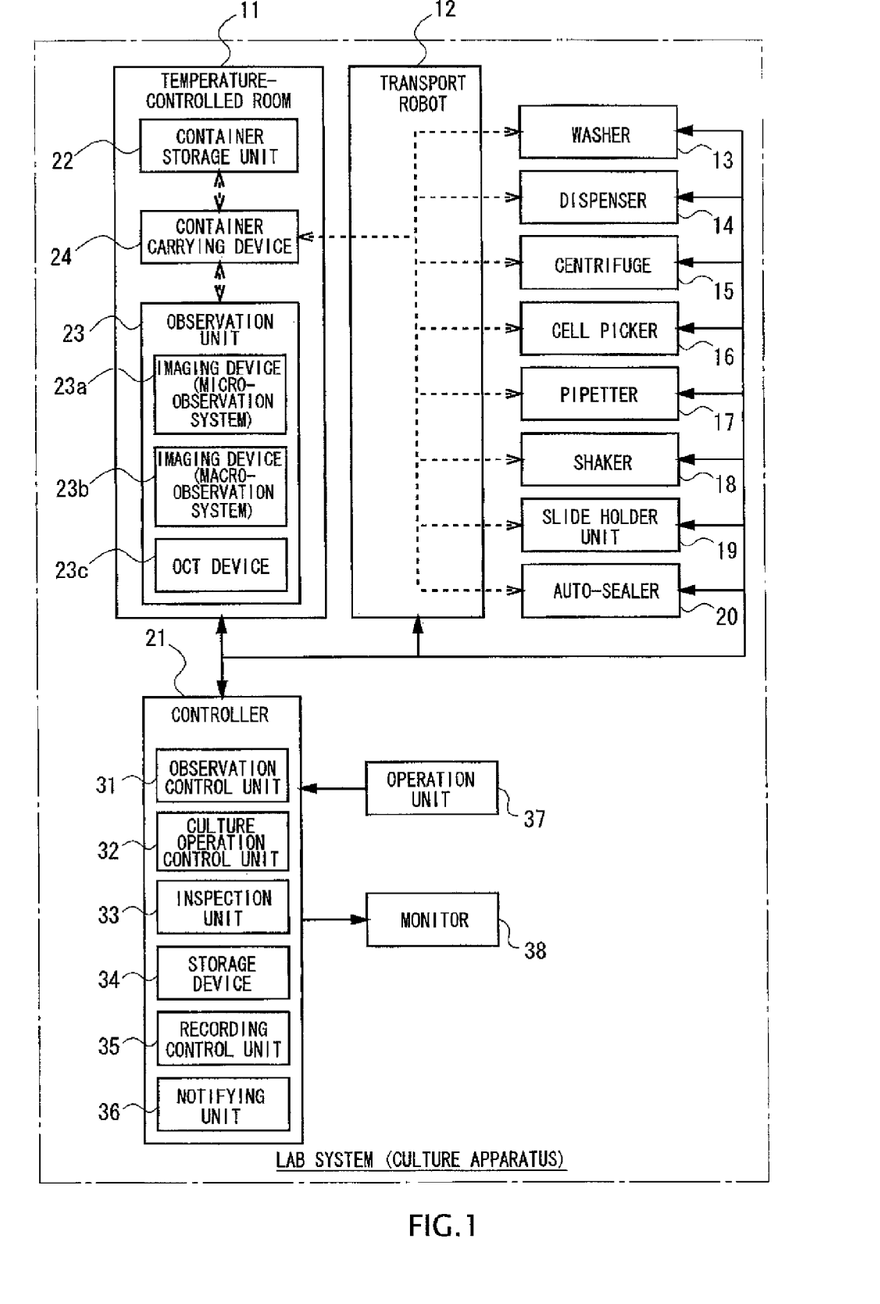
FIG. 1 is a diagram showing an example of the configuration of a culture apparatus according to one embodiment.

FIG. 1 is a diagram showing an example of the configuration of a culture apparatus according to one embodiment. As the culture apparatus of the embodiment, an example of a lab system will be described in which the culture and observation of culture cells and various culture operations on the culture cells are performed.

The lab system includes a temperature-controlled room 11, a transport robot 12, a washer 13, a dispenser 14, a centrifuge 15, a cell picker 16, a pipetter 17, a shaker 18, a slide holder unit 19, an auto-sealer 20, and a controller 21. Here, the temperature-controlled room 11, the transport robot 12, the washer 13, the dispenser 14, the centrifuge 15, the cell picker 16, the pipetter 17, the shaker 18, the slide holder unit 19, and the auto-sealer 20 are each connected to the controller 21 by wiring.

Here, in the present specification, the respective operations of the washer 13, the dispenser 14, the centrifuge 15, the cell picker 16, the pipetter 17, the shaker 18, the slide holder unit 19, and the auto-sealer 20 are referred to as the culture operation. Moreover, in the figures of the present specification, the connection of the wiring is indicated by solid-line arrows, and the flow of the transport of a culture container is indicated by broken-line arrows.

In the temperature-controlled room 11, the culture container that cultures culture cells is stored. The internal atmosphere of the temperature-controlled room 11 is maintained by an integral environment control apparatus (not shown) to be an environment (for example, an atmosphere where its temperature is 37° C., its humidity is 90% and its concentration of $CO_2$ is 5%) suitable for culturing the cells, and is also maintained to be high cleanliness so as to prevent contamination. In the culture container, the culture cells are held together with a culture medium.

Moreover, within the temperature-controlled room 11, a container storage unit 22 (stocker) that stores a plurality of culture containers, an observation unit 23 that is an example of an imaging unit, and a container carrying device 24 are arranged.

Here, the observation unit 23 is an electronic camera module for observing culture cells and the like under the environment of the temperature-controlled room 11. The observation unit 23 of the embodiment includes: a micro-observation system imaging device 23a that images the culture cells through a transmission type microscope (for example, a phase-contrast microscope); and a macro-observation system imaging device 23b that can image the entire culture container in an overhead view. The observation unit 23 can also capture an inspection image for determining whether or not the culture operation is appropriate. Images captured by the micro-observation system and macro-observation system imaging devices 23a and 23b are each input to the controller 21.

The observation unit 23 of the embodiment further includes an OCT device 23c by optical coherence tomography (OCT). Since the OCT device 23c uses light of a large wavelength width as a probe, the OCT device 23c can observe the three-dimensional structure of an item to be observed transparent to the light without dyeing and without invasion.

The container carrying device 24 delivers the culture container between the container storage unit 22 and the observation unit 23 by control of the controller 21. Thus, it is possible to perform time-lapse observation on the culture container stored in the storage unit of the temperature-controlled room 11 at predetermined time intervals. The container carrying device 24 also delivers the culture container between the container carrying device 24 and the transport robot 12 by control of the controller 21. Thus, it is possible to carry-out/carry-in the culture container from/to the temperature-controlled room 11.

The environment conditions of the atmosphere outside the temperature-controlled room 11 in the lab system may not be equivalent to those of the atmosphere in the temperature-controlled room 11, but the parameters of the environment conditions may be brought close to the internal atmosphere of the temperature-controlled room 11.

By control of the controller 21, the transport robot 12 carries the culture container between the individual units (the washer 13, the dispenser 14, the centrifuge 15, the cell picker 16, the pipetter 17, the shaker 18, the slide holder unit 19, and the auto-sealer 20), which perform the culture operation within the lab system, and the temperature-controlled room 11. The transport robot 12 also carries-out/carries-in the culture container from/to the lab system to/from the outside.

The washer 13 is a unit that is mainly used for culture medium replacement in the culture container, and sucks the old culture medium from the culture container. The dispenser 14 is a unit that is mainly used for culture medium replacement in the culture container, and injects a new culture medium into the culture container. The dispenser 14 can be also used for injection of a drug into the culture container.

As an example, the washer 13 and the dispenser 14 have substantially the same configuration, and each include a drive unit that drives a disposable syringe chip to perform culture medium absorption or culture medium injection and a mounting and dismounting mechanism that mounts and dismounts the above described syringe chip to and from the drive unit.

The centrifuge 15 is a device that separates the culture cells from various types of solutions by centrifugal force. As an example, the centrifuge 15 is used to separate, when an unfreezing process is performed on frozen cells, the cells and a supernatant or to remove trypsin when the cells are cultured.

The cell picker 16 is a device that picks and takes out an arbitrary colony from the culture container. For example, the cell picker 16 may be used at the time of the passage of the culture cells.

The pipetter 17 is a device for spraying the cells over a new culture container. For example, the pipetter 17 is used, at the time of the passage of the culture cells, to spray the culture cells obtained from the picked colony over a new culture container. The pipetter 17 can also be used to spray feeder cells necessary for the culture of iPS cells over the culture container.

The shaker 18 is a device that vibrates the culture container in a substantially horizontal direction to uniformly flatten the cells sprayed within the culture container.

The slide holder unit 19 is a device for supplying an unused culture container to the pipetter 17 or the like. Moreover, the auto-sealer 20 is a device that attaches a seal tape onto the culture container after the culture operation to seal the culture container.

The controller 21 is a computer that comprehensively controls the operation of the lab system and that manages the culture process of the cells in the lab system on an individual culture container basis. The controller 21 includes an observation control unit 31, a culture operation control unit 32, an inspection unit 33, a storage device 34, a recording control unit 35, and a notifying unit 36. An operation unit 37 that receives an operation of a user and a monitor 38 that displays an image and the like are connected to the controller 21.

The observation control unit 31 controls the observation unit 23 and the container carrying device 24 based on a previously recorded schedule, and performs the time-lapse observation on the culture cells held in the culture container.

The culture operation control unit 32 controls, according to the result of the time-lapse observation or an instruction from the user, the individual units that perform the culture operation, and performs events such as the passage and the culture medium replacement of the culture container.

The inspection unit 33 controls the observation unit 23, at least after the culture operation, to capture an inspection image. The inspection unit 33 also functions as a determining unit that analyzes the inspection image to determine whether or not the culture operation is appropriate.

The storage device 34 is a nonvolatile storage medium that stores basic registration information, observation information on the culture container, and culture operation information. The basic registration information, the observation information on the culture container, and the culture operation information are generated one set for each of the culture containers managed in the lab system.

Here, the basic registration information includes attribute information (such as the type of culture cells, the type of culture medium, and the history of the passage) on the culture container; a schedule (such as an interval of the observation and imaging conditions when each observation is performed) of the time-lapse observation on the culture container; and information on determination conditions when the passage, the culture medium replacement, and the like are performed.

Moreover, the observation information on the culture container includes a plurality of observation images acquired in the time-lapse observation targeting a certain culture container, information indicating a time when each observation image is acquired and information on the environment conditions of the temperature-controlled room 11 in an observation period.

In addition, the culture operation information includes historical information on a plurality of culture operations performed in chronological order on a certain culture container and the inspection image acquired in each culture operation. In the historical information described above, information on the types and times of individual culture operations and information indicating whether or not each culture operation is appropriate are stored such that they are associated with each other.

Figure 2:
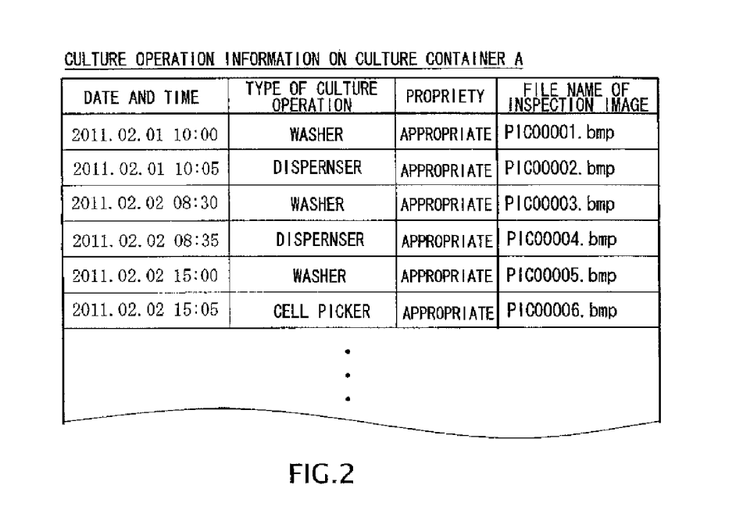
FIG. 2 is a diagram showing an example of historical information of a culture operation on a culture container.

An example of the culture operation information on a certain culture container (culture container A) is shown in FIG. 2 in the form of a table. FIG. 2 shows a state where the history of the culture operation and the file name of the inspection image are recorded in association with each other, each time the culture operation is performed.

The recording control unit 35 records various types of information (the basic registration information, the observation information on the culture container, and the culture operation information) in the storage device 34. In addition, the recording control unit 35 performs falsification prevention processing on the observation information on the culture container and the culture operation information.

The notifying unit 36 outputs a warning to the outside when the inspection unit 33 determines that the culture operation is not appropriate. As an example, the notifying unit 36 outputs a warning display to the monitor 38. Alternatively, the notifying unit 36 may transmit mail to a personal computer (or a mobile computer) of the user. The transmission of the mail described above is performed through an unillustrated communication unit.

As an example of the application of the lab system, a case where iPS cells are cultured will be described below. The outline of the culture process of iPS cells that is being presently examined in a regenerative medicine field is as shown in items (1) to (4) below.

(1) An extraction process of somatic cells (such as blood and skin cells) from a patient (2) A dedifferentiation process into iPS cells (about 1 to 3 weeks)

First, a virus vector, a human artificial chromosome (HAC) vector or the like is used to produce iPS cells by introducing a gene into the somatic cells of the patient. Then, while the cells having the gene introduced therein are cultured, the time-lapse observation is performed about once per day. Then, a colony of the iPS cells is found from an observation image obtained in the time-lapse observation. For example, when it is determined, using, as an index, a fluorochrome attached to a surface antibody or the like, that the dedifferentiation into the IPS cells has been completed, the target colony (the colony of the iPS cells) is collected by pipetting.

(3) A growth process of the iPS cells (from one week to . . . )

The iPS cells obtained in the process of item (2) described above are sprayed over the culture container, and are cultured and grown. In this process, the colonies of the iPS cells are picked up, and the cells obtained by separating the colonies into individual pieces are repeatedly sprayed again over a plurality of culture containers. In this process, based on the result of the time-lapse observation, only the colonies in good condition are selected and picked up.

(4) A differentiation process from the iPS cells (from two weeks to . . . )

The iPS cells grown in the process of item (3) described above are sprayed over the culture container, and a differentiation-inducing reagent is added to perform culture. When it is determined, based on the result of the time-lapse observation, that the target cells are generated, the target cells are extracted, and the culture is completed.

The lab system of the embodiment can be used for the culture of the cells in the processes of items (2) to (4) described above. In the lab system, it is possible to perform the time-lapse observation on the culture cells and the culture operation (the culture medium replacement and the passage) on the culture cells. The lab system can simultaneously perform the culture process of cells on a plurality of culture containers.

Figure 3:
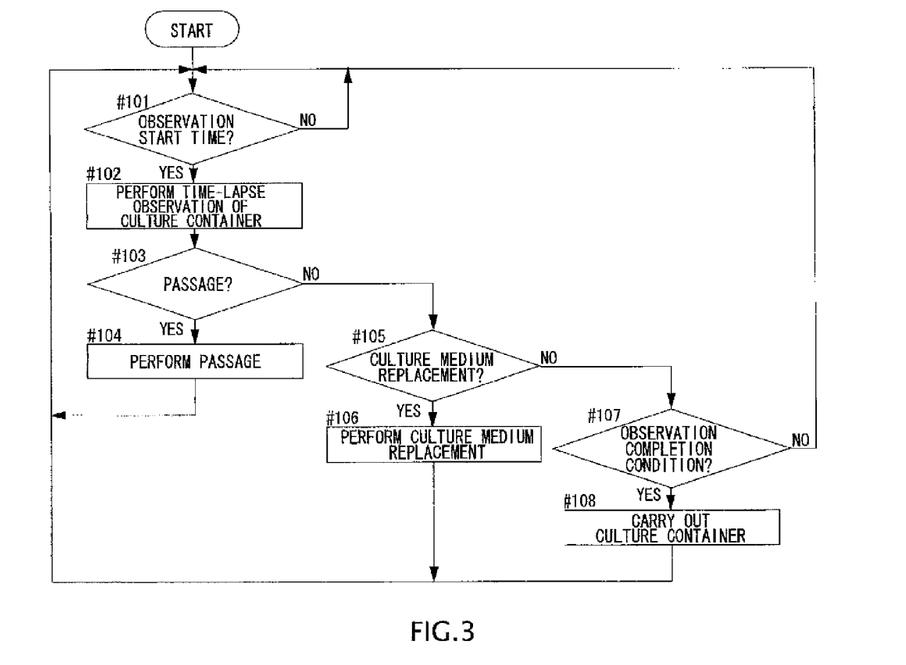
FIG. 3 is a flowchart showing an example of the operation of a lab system according to one embodiment.

An example of the operation of the lab system according to the embodiment will now be described with reference to FIG. 3. In the example of FIG. 3, a description will be given on the assumption that the culture container holding the cells is previously stored in the temperature-controlled room 11 and that the basic registration information is previously registered in the storage device 34.

Step #101: The observation control unit 31 references the basic registration information (the schedule of the time-lapse observation) in the storage device 34, and determines whether or not a time when any culture container starts to be observed is reached. If the above described requirement is satisfied (on the side of YES), the process moves to #102. On the other hand, if the above described requirement is not satisfied (on the side of NO), the observation control unit 31 is placed on standby until a time when any culture container starts to be observed.

Step #102: The observation control unit 31 performs the time-lapse observation on the culture container.

The observation control unit 31 in step #102 controls the container carrying device 24 to carry the culture container, which is the observation target, from the container storage unit 22 to the observation unit 23. Then, the observation control unit 31 controls the observation unit 23 to capture the observation image of the culture cells with the micro-observation system imaging device 23*a* and to capture the observation image of the culture cells with the OCT device 23*c*. The observation control unit 31 in step #102 may capture the entire observation image of the culture container with the macro-observation system imaging device 23*b*. Thereafter, the recording control unit 35 updates the observation information on the culture container of the storage device 34. Specifically, the recording control unit 35 associates the observation information on the culture container subjected to the time-lapse observation with the observation image captured in #102, and records the observation information and the observation image.

Step #103: The culture operation control unit 32 determines whether or not to perform the passage on the culture container observed in #102.

As an example, the culture operation control unit 32 in step #103 analyzes the micro-observation system observation image or the observation image with the OCT. Then, the culture operation control unit 32 determines to perform the passage, when the occupancy of a cell region in the culture container is equal to or more than a threshold value (when it is close to a confluent state).

If the above described requirement is satisfied (on the side of YES), the process moves to #104. On the other hand, if the above described requirement is not satisfied (on the side of NO), the process moves to #105.

Step #104: The culture operation control unit 32 controls the washer 13, the cell picker 16, the dispenser 14, the pipetter 17, and the like to perform the passage on the culture cells. As an example, the culture operation in #104 will be performed as follows.

The washer 13 first sucks the old culture medium from the culture container in which the passage is performed. The cell picker 16 picks the colonies of the culture cells from the culture container in which the passage is performed. At this time, trypsin processing may be performed to separate the cells from the culture container. Then, the dispenser 14 injects the culture medium into a new culture container supplied from the slide holder unit 19. Then, the pipetter 17 separates, to some degree, the picked colonies into individual pieces, and sprays the culture cells over the new culture container. Thereafter, the culture container is agitated with an agitator so as not to spill the culture medium, and thus the cells are made uniform. The culture container after the passage is stored in the temperature-controlled room 11.

Here, in each culture operation with respect to the passage described above, an inspection process (FIG. 4) for the culture operation, which will be described later, is performed.

Moreover, when the passage is performed in #104, the basic registration information corresponding to the culture container after the passage is registered in the storage device 34 by the recording control unit 35. Here, the recording control unit 35 records the history of the current passage in the basic registration information, and has the basic registration information on the culture container before the passage on the other items taken over. After the above described processing, the process returns to #101, and the processing is repeated.

Step #105: The culture operation control unit 32 analyzes the observation image to determine whether or not the culture medium replacement is needed. As an example, the culture operation control unit 32 preferably determines, based on the color of a pH reagent added to the culture medium of the observation image, whether or not the culture medium replacement is needed.

If the above described requirement is satisfied (on the side of YES), the process moves to #106. On the other hand, if the above described requirement is not satisfied (on the side of NO), the process moves to #107.

Step #106: The culture operation control unit 32 controls the washer 13 and the dispenser 14 to perform the culture medium replacement.

The washer 13 first sucks the old culture medium from the culture container. Then, the dispenser 14 injects a new culture medium into the culture container. The culture container after the culture medium replacement is stored in the temperature-controlled room 11. Then, the process returns to #101, and the processing is repeated.

In each of the culture operations with respect to the culture medium replacement described above, the inspection process (FIG. 4) in the culture operation, which will be described later, is performed.

Step #107: The culture operation control unit 32 analyzes the micro-observation system observation image or the observation image with the OCT, and determines whether or not culture completion conditions are satisfied. Specifically, the culture operation control unit 32 determines that the culture completion conditions are satisfied, if the culture cells are brought into the desired state (for example, if dedifferentiation into iPS cells can be performed or if iPS cells can be differentiation-induced into the desired cells). For example, the culture operation control unit 32 preferably determines, according to the morphological characteristics (such as the size of the cells, the shape of the cells and whether or not apoptosis occurs) of the culture cells included in the observation image and a reaction between the cells and a marker, whether or not the culture cells are in the desired state. When the differentiation induction into heart muscle cells is performed, if it is possible to detect the repeated contraction movement (the pulsation of the heart muscle cells) of the culture cells from the observation images of a plurality of frames, the culture operation control unit 32 preferably determines that the culture completion conditions are satisfied.

If the above described requirement is satisfied (on the side of YES), the process moves to #108. On the other hand, if the above described requirement is not satisfied (on the side of NO), the process returns to #101, and the processing is repeated.

Step #108: The culture operation control unit 32 controls the transport robot 12 to carry out the culture container from the lab system. As with the case of the passage of #104, the culture operation control unit 32 may pick only the culture cells in the desired state with the cell picker 16 and continue the culture of the cells in another culture container. After the processing described above, the process returns to #101, and the processing is repeated. Now, the description of the flowchart of FIG. 3 has been completed.

Figure 4:
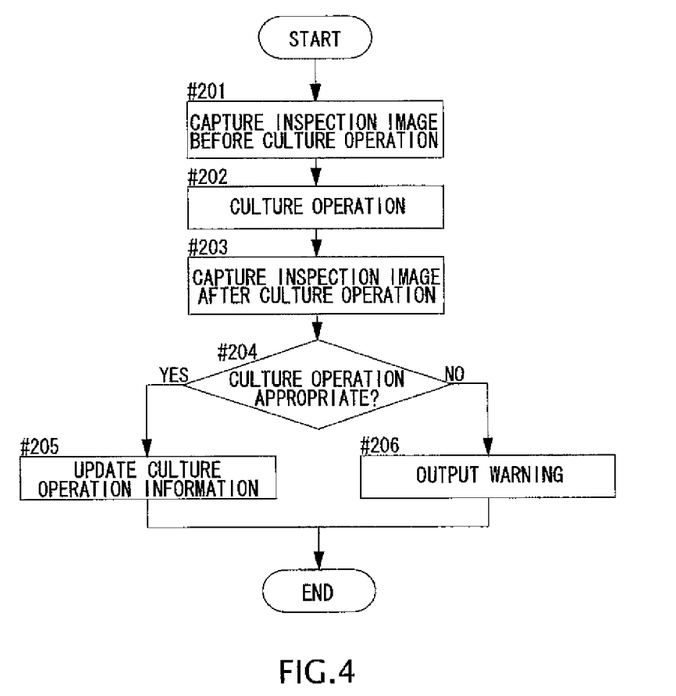
FIG. 4 is a flowchart showing an example of an inspection step in the culture operation in the lab system according to one embodiment.

The inspection process of the culture operation in the lab system of the embodiment will now be described with reference to the flowchart of FIG. 4. The processing in the flowchart of FIG. 4 is performed when the operation of any one of the washer 13, the dispenser 14, the centrifuge 15, the cell picker 16, the pipetter 17, the shaker 18, the slide holder unit 19, and the auto-sealer 20 is performed.

Step #201: The culture operation control unit 32 controls the transport robot 12 and the container carrying device 24 to carry the culture container before the culture operation to the observation unit 23. Then, the inspection unit 33 controls the observation unit 23 to capture the inspection image showing the state of the culture container or the like before the culture operation.

Here, the processing in #201 may be omitted depending on the type of culture operation. When the time-lapse observation is performed before the culture operation, the inspection image in #201 may be captured.

Step #202: The culture operation control unit 32 controls the transport robot 12 and the container carrying device 24 to carry the culture container to the unit that performs the culture operation. Then, the culture operation control unit 32 controls the unit that performs the culture operation to perform the culture operation.

Step #203: The culture operation control unit 32 controls the transport robot 12 and the container carrying device 24 to carry the culture container after the culture operation to the observation unit 23. Then, the inspection unit 33 controls the observation unit 23 to capture the inspection image.

Step #204: The inspection unit 33 analyzes the above described inspection image (#201 and #203) to determine whether or not the culture operation is appropriate. If the above described requirement is satisfied (on the side of YES), the process moves to #205. On the other hand, if the above described requirement is not satisfied (on the side of NO), the process moves to #206.

For example, the inspection unit 33 of the embodiment determines, in the following manner, whether or not each culture operation is appropriate.

(a) An Example of the Inspection with the Washer

In the culture operation with the washer 13, the inspection unit 33 omits the processing in #201, and in #203, the macro-observation system imaging device 23*b* captures the inspection image of the culture container.

The inspection unit 33 in #204 determines, from the inspection image after the suction of the culture medium, whether or not the culture medium is left within the culture container. For example, the inspection unit 33 focuses on the color within the culture container in the inspection image, and determines whether or not the culture medium (the portion of the color of the pH reagent) is left. Specifically, if a ratio of a color region (the colored area) to the area of the bottom of the culture container is determined to be a predetermined value or more, the inspection unit 33 determines that the culture medium is left within the culture container.

The inspection unit 33 may also focus on the liquid surface height to determine whether or not the culture medium is left. For example, it is possible to estimate the liquid surface height of the culture medium, based on the image of the culture container, by utilizing a parallax between the outline of the liquid surface and the outline of the bottom surface of the culture container. The inspection unit 33 compares the estimated height and the standard value to determine whether or not the culture medium is left.

Then, if the culture medium is left, the inspection unit 33 determines that the culture operation with the washer 13 is not appropriate.

(b) An Example of the Inspection with the Dispenser

In the culture operation with the dispenser 14, the inspection unit 33 omits the processing in #201, and in #203, the macro-observation system imaging device 23*b* captures the inspection image of the culture container.

The inspection unit 33 in #204 determines, from the inspection image after the suction of the culture medium, whether or not the culture medium is left within the culture container. A method of determining whether or not the culture medium is left is the same as (a) described above, and thus its description will not be repeated.

Then, if the culture medium is not left, the inspection unit 33 determines that the culture operation with the dispenser 14 is not appropriate.

In the culture operation with the dispenser 14, when a predetermined time period has elapsed after the culture operation, the inspection unit 33 may further capture the inspection image with the micro-observation system imaging device 23*a*. Then, the state (such as the life or death and the activation) of the culture cells is checked with the above described inspection image, and whether or not an appropriate culture medium is injected with the dispenser 14 into the culture container may be determined.

(c) An Example of the Inspection with the Centrifuge

In the culture operation with the centrifuge 15, in #201 and #203, the macro-observation system imaging device 23*b* captures the inspection image of the culture container.

The inspection unit 33 in #204, for example, counts the number of cells included in the inspection image in #201 and #203, and determines whether or not the number of cells in both cases is changed by a threshold value or more. Then, if the number of cells is changed by the threshold value or more, the inspection unit 33 determines that the culture operation with the centrifuge 15 is not appropriate.

In the culture operation with the centrifuge 15, when a predetermined time period has elapsed after the culture operation, the inspection unit 33 may further capture the inspection image with the micro-observation system imaging device 23*a*. Then, the state (such as the life or death and the activation) of the culture cells is checked with the inspection image, and whether or not the culture operation is appropriate may be determined by the presence or absence of damage to the cells with the centrifuge 15.

(d) An Example of the Inspection with the Cell Picker

In the culture operation with the cell picker 16, in #201 and #203, the macro-observation system imaging device 23*b* captures the inspection image of the culture container.

The inspection unit 33 in #204, for example, determines, with the inspection image in #201 and #203, the presence or absence of colonies that are the target to be picked. For example, the inspection unit 33 extracts the outline image of the colonies based on the inspection image, and calculates, from the extracted outline image, information on the shape of the colonies, information on the area of the colonies, and information on the brightness distribution of the colonies. For example, in the normal colonies, it is possible to narrow, from the information described above, the target to be picked by the degree of deformation, that is, how much the colonies in the shape information are deformed with respect to a true circle. Alternatively, it is possible to use, based on the area information, the target to be picked that is large as compared with the reference area. Alternatively, it is possible to extract the target to be picked that has a predetermined degree of uniformity by obtaining the uniformity of the brightness distribution based on the brightness distribution information.

Then, if in the inspection image in #203, part or all of the colonies that are the target to be picked are present, the inspection unit 33 determines that the culture operation with the cell picker 16 is not appropriate.

(e) An Example of the Inspection with the Pipetter

In the culture operation with the pipetter 17, the inspection unit 33 omits the processing in #201, and in #203, when a predetermined time period has elapsed (for example, when the sprayed cells adhere to the culture container) after the culture operation, the micro-observation system imaging device 23*a* captures the inspection image of the culture container.

Then, the inspection unit 33 in #204 checks the form of the culture cells with the inspection image. If the cells are not properly seeded, the inspection unit 33 determines that the culture operation with the pipetter 17 is not appropriate.

(f) An Example of the Inspection with the Shaker

In the culture operation with the shaker 18, the inspection unit 33 omits the processing in #201, and in #203, the macro-observation system imaging device 23*b* captures the inspection image of the culture container.

Then, the inspection unit 33 in #204 divides the above described inspection image into a plurality of regions, and determines the secondary moment of the image for each divided region. If a region where the secondary moment of the image is locally large is present (if a region where the cells are gathered is present), the inspection unit 33 determines that the culture operation with the shaker 18 is not appropriate.

(g) An Example of the Inspection with the Slide Holder Unit

In the culture operation with the slide holder unit 19, the inspection unit 33 omits the processing in #201, and in #203, the macro-observation system imaging device 23*b* captures the inspection image of the culture container. Then, if the culture container supplied from the slide holder unit 19 is not present within the image, the inspection unit 33 in #204 determines that the culture operation with the slide holder unit 19 is not appropriate, (h) An Example of the Inspection with the Auto-Sealer In the culture operation with the auto-sealer 20, the inspection unit 33 omits the processing in #201, and in #203, the macro-observation system imaging device 23*b* captures the inspection image of the culture container. Then, if the culture container is not sealed, the inspection unit 33 in #204 determines that the culture operation with the auto-sealer 20 is not appropriate.

Step #205: The recording control unit 35 updates the culture operation information in the storage device 34. Specifically, the recording control unit 35 adds information (the type and time of culture operation, whether or not the culture operation is appropriate and the inspection image) with respect to the current culture operation to the culture operation information corresponding to the culture container where the culture operation is performed. At this time, the recording control unit 35 performs the falsification prevention processing (for example, the embedding of digital watermark or the encryption) on the culture operation information. Thereafter, the inspection unit 33 completes the processing in the inspection process.

Step #206: The notifying unit 36 outputs, to the monitor 38, a warning indicating that the current culture operation is not appropriate. In the processing in #206, the recording control unit 35 may add the information on the current culture operation to the culture operation information in the storage device 34. Thereafter, the inspection unit 33 completes the processing in the inspection process. Now, the description of the flowchart of FIG. 4 has been completed.

The actions and effects of the lab system of the embodiment will be described below.

Under control of the controller 21, the lab system of the embodiment performs the cell culture in the temperature-controlled room 11, the time-lapse observation of the cells, and the culture operation with respect to the passage and the culture medium replacement. Hence, with the lab system of the embodiment, it is possible to significantly save labor in the culture process of the cells. With the lab system of the embodiment, it is possible to reduce human errors in the culture process and also level off the culture process, with the result that it is easy to stabilize the quality of the culture cells.

Moreover, in the lab system of the embodiment, when the culture operation with respect to the passage and the culture medium replacement is performed, the inspection image is captured, and whether or not the culture operation is appropriate is determined based on the inspection image. Thus, the lab system of the embodiment can manage whether or not the culture operation is appropriate in the culture process.

Moreover, the recording control unit 35 of the embodiment records, in the storage device 34, the historical information indicating whether or not a plurality of culture operations performed in chronological order in the same culture container is appropriate. The above described historical information functions to guarantee that the culture operation is properly performed on a certain culture container. Hence, in the lab system of the embodiment, it is possible to guarantee, with the historical information, the quality of the culture cells obtained in the culture process.

For example, in a regenerative medicine field, since culture cells are used as drugs that work in the body, it is assumed that the management of the cells conforms to standards (GMP: Good Manufacturing Practice) of the manufacturing management and the quality management of drugs and quasi-drugs. In such a case, although it is essential to verify whether or not each culture operation is appropriate, the lab system of the embodiment can satisfy the management of each culture operation at a high level.

Moreover, in the embodiment, historical information on a plurality of culture containers is verified in a cross-sectoral manner, and thus it is also possible to evaluate the entire culture environment of the lab system. For example, in the certification review of industrial standards on the management of the culture process, the above described historical information can be utilized as useful material.

Moreover, since the recording control unit 35 of the embodiment records the historical information and inspection information in association with each other in the storage device 34, the historical information is easily verified. Moreover, since the recording control unit 35 of the embodiment performs the falsification prevention processing on the culture operation information, it is possible to more increase the reliability of the culture operation information including the historical information.

In the quality management of the culture cells in the culture process, not only managing states of the culture cells themselves but also managing whether or not various culture operations (such as culture medium replacement and passage) performed in the culture process are appropriate is important.

<Description of Another Embodiment>

Figure 5:
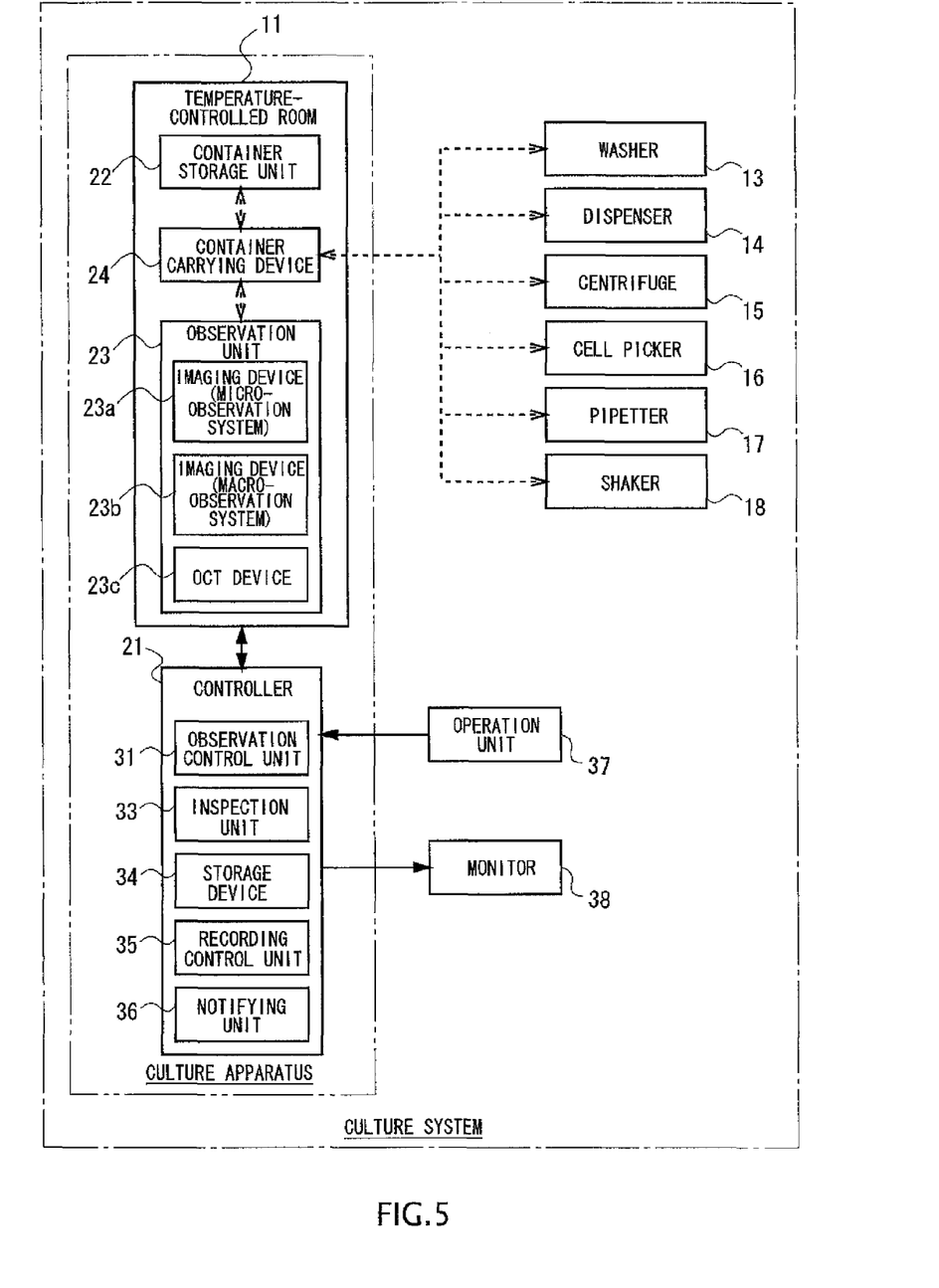
FIG. 5 is a diagram showing an example of a culture system according to another embodiment.

FIG. 5 is a diagram showing an example of a culture system of another embodiment. The another embodiment is a variation of the embodiment described above; in the another embodiment, the same elements as the embodiment are identified with the same symbols, and their description will not be repeated.

The culture system of the another embodiment includes a culture apparatus incorporating the temperature-controlled room 11 and the controller 21 and a plurality of units (the washer 13, the dispenser 14, the centrifuge 15, the cell picker 16, the pipetter 17, and the shaker 18) that performs the culture operation. The above described temperature-controlled room 11 includes the container storage unit 22, the observation unit 23, and the container carrying device 24. The controller 21 includes the observation control unit 31, the inspection unit 33, the storage device 34, the recording control unit 35, and the notifying unit 36. The temperature-controlled room 11, the operation unit 37, and the monitor 38 are connected to the controller 21.

In the another embodiment, the cell culture apparatus and the units (13 to 18) that perform the culture operation are individually operated. In the another embodiment, delivering of the culture container between the units is performed, for example, manually. Further, the controller 21 of the another embodiment controls the cell culture in the temperature-controlled room 11, the time-lapse observation on the cells with the observation unit 23 and the inspection process on the culture operation with the observation unit 23.

As an example, in the inspection process on the culture operation in the another embodiment, at least after the culture operation, the culture container is carried into the temperature-controlled room 11. The inspection unit 33 controls the observation unit 23 to capture the inspection image, and in the same manner as in #204 described above, analyzes the inspection image to determine whether or not the culture operation is appropriate.

If the culture operation is determined to be appropriate, the recording control unit 35 adds, in the same manner as in #205 described above, information on the current culture operation to the culture operation information in the storage device 34. On the other hand, if the culture operation is determined not to be appropriate, the notifying unit 36 outputs a warning indicating that the current culture operation is not appropriate to the monitor 38.

In the another embodiment, when the culture operation with respect to the passage and the culture medium replacement is performed, the cell culture apparatus captures the inspection image, and determines whether or not the culture operation is appropriate based on the inspection image. Moreover, the recording control unit 35 of the another embodiment records, in the storage device 34, the historical information indicating whether or not a plurality of culture operations performed in a chronological manner in the same culture container is appropriate.

Hence, in the another embodiment, it is also possible to manage whether or not the culture operation in the culture process is appropriate. In the another embodiment, it is also possible to guarantee, with the historical information, the quality of the culture cells obtained in the culture process.

<Supplemental Matter of the Embodiment>

(Supplemental matter 1): In the embodiment described above, apart from the observation unit 23 performing the time-lapse observation, the imaging unit that captures the inspection image may be provided. Note that, the above described imaging unit may be arranged outside the temperature-controlled room 11.

(Supplemental matter 2): In the embodiment described above, the observation unit 23 may further include the imaging device that observes the cells with a confocal fluorescence microscope having a laser light source and a confocal optical system.

(Supplemental matter 3): In the embodiment described above, the culture operation control unit 32 may start the passage according to the instruction of the user. Moreover, in the embodiment described above, the culture operation control unit 32 may perform the culture medium replacement at regular intervals.

(Supplemental matter 4): Although in the embodiment described above, the example where the observation control unit 31, the culture operation control unit 32, the inspection unit 33, the recording control unit 35, and the notifying unit 36 of the controller 21 are realized by hardware has been described, the functions of these units may be realized by computer programs. In such a case, the programs are preferably recorded in, for example, the storage device 34.

(Supplemental matter 5): In the embodiment described above, the recording control unit 35 may record, in the storage device 34, the information on the date and time of and the observation image of the time-lapse observation and the culture operation information (FIG. 2) in a unified way.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A culture apparatus, comprising:
   a culture room for culturing cells under a predetermined culture environment;
   an imaging device that is configured to capture an inspection image showing one of a state of a culture container that holds the cells or a state of the cells; and
   a controller that:
      detects completion of a culture operation of at least one peripheral device used in the culture operation of the cells,
      controls the imaging device to capture the inspection image after the completion of the culture operation, and
      analyzes the inspection image obtained after the completion of the culture operation to determine whether or not the culture operation by the at least one peripheral device is appropriate,
   wherein when the at least one peripheral device comprises a washer:
      (a) the culture operation comprises sucking the culture medium from the culture container; and
      (b) the analysis of the inspection image comprises determining whether or not the culture medium is left within the culture container by either:
         (i) measuring the ratio of the area of a color region to the area of the bottom of the culture container and comparing it to a predetermined value; or
         (ii) estimating a liquid surface height of the culture medium by using a parallax between an outline of the liquid surface and an outline of the bottom surface of the culture container and comparing the estimated liquid surface height and a standard value,
   wherein when the at least one of the peripheral device comprises a dispenser:
      (a) the culture operation comprises dispensing a culture medium into the culture container; and (b) the analysis of the inspection image comprises either:
  (i) determining whether or not the culture medium is left within the culture container by measuring the ratio of the area of a color region to the area of the bottom of the culture containing and comparing it to a predetermined value;
  (ii) determining whether or not the culture medium is left within the culture containing by estimated a liquid surface height of the culture medium by using a parallax between an outline of the liquid surface and an outline of the bottom surface of the culture container and comparing the estimated liquid surface height and a standard value; or
  (iii) determining whether or not an appropriate culture medium is left within the culture container by determining the life, death or activation of the culture cells in the image,
wherein when the at least one of the peripheral device comprises a centrifuge:
  (a) the culture operation comprises centrifuging the culture container; and
  (b) the analysis of the inspection image comprises either:
    (i) counting the number of cells in the inspection image and determining whether or not a number of cells in the image has changed by a threshold value or greater than the threshold value; or
    (ii) determining the presence or absence of damage to the cells by determining the life, death or activation of the culture cells in the image,
wherein when the at least one of the peripheral device comprises a cell picker:
  (a) the culture operation comprises picking part or all of target colonies of the culture cells; and
  (b) the analysis of the inspection image comprises extracting the outline image of the colonies from the image and calculating information of the shape of the colonies, information on the area of the colonies, or information on the brightness distribution of the colonies in the image;
wherein when the at least one of the peripheral device comprises a pipette:
  (a) the culture operation comprises spraying previously picked colonies into the culture container; and
  (b) the analysis of the inspection image comprises determining the form of the culture cells in the image,
wherein when the at least one of the peripheral device comprises a shaker:
  (a) the culture operation comprises shaking the culture container; and
  (b) the analysis of the inspection image comprises dividing the image into a plurality of regions and determining the secondary moment of the image for each divided region,
wherein when the at least one of the peripheral device comprises a slide holder unit:
  (a) the culture operation comprises supplying an unused culture container; and
  (b) the analysis of the inspection image comprises determining that the slide holder unit is not present in the image, and
wherein when the at least one of the peripheral device comprises an auto-sealer:
  (a) the culture operation comprises sealing the culture container; and
  (b) the analysis of the inspection image comprises determining that the culture container is not sealed in the image.

2. The culture apparatus according to claim 1, wherein the controller is configured to change a method of analyzing the inspection image for each type of culture operations.

3. The culture apparatus according to claim 2, wherein the culture operation comprises processing on one of culture medium replacement or passage.

4. The culture apparatus according to claim 1, wherein the controller is further configured to:
record in a storage medium historical information indicating whether or not a plurality of culture operations performed in chronological order on the culture container being the same is appropriate.

5. The culture apparatus according to claim 4, wherein the controller is configured to record in the storage medium the inspection image and the historical information in association with each other.

6. The culture apparatus according to claim 4, wherein the controller is configured to perform falsification prevention processing on the historical information.

7. The culture apparatus according to claim 1, wherein the controller is further configured to output a warning to outside of the culture apparatus when the culture operation is determined not to be appropriate.

8. The culture apparatus according to claim 1, wherein the culture room is a temperature-controlled room in which an internal atmosphere is maintained at a predetermined environment condition and that holds the culture container.

9. The culture apparatus according to claim 1, wherein the controller is further configured to operate at least one peripheral device that is used in a culture operation of the cells.

10. The culture apparatus according to claim 1, wherein the controller is further configured to control the culture room and the peripheral device.

11. The culture apparatus according to claim 1, further comprising a non-transitory storage medium storing a program that causes the controller to perform the detecting, the controlling, and the analyzing.

12. The culture apparatus according to claim 1, further comprising
a carrying device configured to deliver the culture container between the peripheral device and the culture apparatus.

13. The culture apparatus according to claim 1, wherein the peripheral device performs a plurality of mutually different culture operations and the controller is further configured to determine the propriety of the plurality of mutually different culture operations with the imaging device.

14. The culture apparatus according to claim 1, wherein the controller is further configured to record in a storage medium historical information indicating a plurality of culture operations performed in chronological order on the culture container being the same is appropriate.

15. The culture apparatus according to claim 1, wherein the controller is further configured to record in a storage medium historical information indicating a plurality of culture operations performed in chronological order on the culture container being the same is not appropriate.

16. The culture apparatus according to claim 1, wherein the controller is connected to the peripheral device.

17. The culture apparatus according to claim 1, wherein the imaging device is arranged within the culture room.

18. The culture apparatus according to claim 1, wherein the peripheral device is arranged outside of the culture room.

19. The culture apparatus according to claim 1, wherein the controller controls the imaging device to capture the inspection image after the completion of the culture operation and before a process of growing or differentiating the cells by culturing in the culture room using the cells that had the culture operation performed thereon.

20. The culture apparatus according to claim 1, wherein the controller controls the imaging device to capture the inspection image after the completion of the culture operation and before performing a time-lapse observation on the cells that had the culture operation performed thereon.

21. A culture operation management method being applied to a culture apparatus system recited in claim 1, the method comprising:
- performing a culture operation with the at least one peripheral device;
- capturing, with the imaging device, the inspection image, wherein the inspection image is obtained after completion of the culture operation; and
- analyzing the inspection image obtained after completion of the culture operation to determine whether or not the culture operation is appropriate.

* * * * *